United States Patent [19]

Abou-Gharbia et al.

[11] Patent Number: 4,672,117
[45] Date of Patent: * Jun. 9, 1987

[54] ANTIPSYCHOTIC GAMMA-CARBOLINES

[75] Inventors: Magid A. Abou-Gharbia, Brandywood, Del.; Usha R. Patel, King of Prussia; Reinhardt P. Stein, Audubon, both of Pa.

[73] Assignee: American Home Products Corporation, New York, N.Y.

[*] Notice: The portion of the term of this patent subsequent to Jan. 13, 2004 has been disclaimed.

[21] Appl. No.: 776,349

[22] Filed: Sep. 16, 1985

[51] Int. Cl.$^4$ .................. C07D 401/06; C07D 471/04; C07D 241/36
[52] U.S. Cl. ................................ 544/405; 544/353; 544/354; 546/86; 546/87
[58] Field of Search ..................... 546/86, 87; 544/353, 544/354, 405

[56] References Cited

U.S. PATENT DOCUMENTS

| | | | |
|---|---|---|---|
| 3,502,688 | 3/1970 | Berger et al. | 546/86 |
| 3,522,262 | 7/1970 | Berger et al. | 546/86 |
| 4,001,263 | 1/1977 | Plattner et al. | 546/86 |
| 4,224,329 | 9/1980 | Welch, Jr. | 546/86 |

Primary Examiner—Henry R. Jiles
Assistant Examiner—J. Richter
Attorney, Agent, or Firm—Richard K. Jackson

[57] ABSTRACT

The compounds:

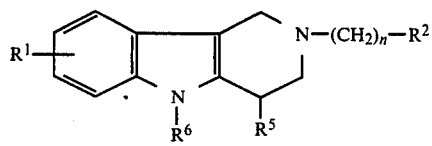

in which
  $R^1$ is hydrogen, halogen, hydroxy, or alkyl;
  $R^2$ is substituted or unsubstituted pyridinyl, pyrazinyl, quinolinyl or quinoxalinyl and said substituents are alkyl, alkoxy, alkoxycarbonyl, halogen, cyano or nitro;
  $R^5$ and $R^6$ are, independently, hydrogen, alkyl, phenyl, halophenyl, methylphenyl, trifluoromethylphenyl, cyanophenyl or nitrophenyl; with the proviso that one of $R^5$ and $R^6$ is other than hydrogen;
  and n is an integer from 1 to 7;

or a pharmaceutically acceptable salt thereof, are antipsychotic and anxiolytic agents.

10 Claims, No Drawings

4,672,117

ANTIPSYCHOTIC GAMMA-CARBOLINES

BACKGROUND OF THE INVENTION

Gamma-carbolines possessing central nervous system activity are known. Representative of the compounds found in the literature are those disclosed by U.S. Pat. Nos. 4,001,263, Plattner et al., and 4,224,329, Welch, as 2-substituted-5-aryl-tetra- and hexahydro-pyrido[4,3-b]indoles. Each reference discloses preferred phenyl-(oxy or oxo)alkyl substitution in 2-position.

DESCRIPTION OF THE INVENTION

In accordance with this invention there is provided a group of tetrahydro-2-heterocyclolalkyl-pyrido[4,3-b]indoles which possess antipsychotic and anxiolytic properties useful in the treatment of psychological disorders such as paranoia and schizophrenia and states of anxiety.

The compounds of this invention present the structural formula:

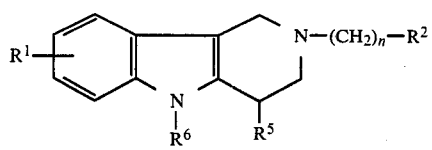

in which
$R^1$ is hydrogen, halogen, hydroxy or alkyl of 1 to 6 carbon atoms;
$R^2$ is

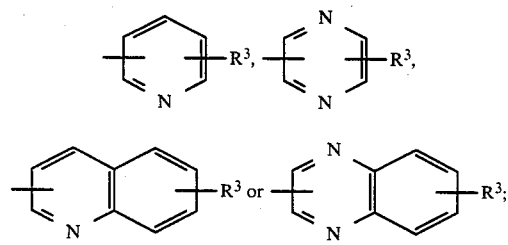

where $R^3$ is hydrogen, alkyl of 1 to 6 carbon atoms, alkoxy of 1 to 6 carbon atoms, $-CO_2R^4$ where $R^4$ is alkyl of 1 to 6 carbon atoms halogen, cyano or nitro;
$R^5$ is hydrogen, alkyl of 1 to 6 carbon atoms, phenyl, or phenyl substituted by a halogen, methyl, trifluoromethyl, cyano or nitro group;
$R^6$ is hydrogen, phenyl, or phenyl substituted by a methyl, ethyl, methoxy, ethoxy, halogen, trifluoromethyl, cyano or nitro group; with the proviso that one of $R^5$ and $R^6$ is other than hydrogen;
and n is one of the integers from 1 to 7;
or a pharmaceutically acceptable salt thereof.

Preferred among the compounds embraced by the foregoing genus are those of the formula:

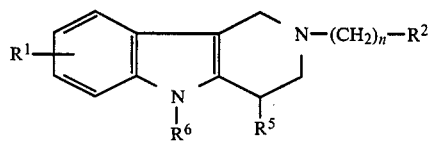

in which
$R^1$ is hydrogen or halogen;
$R^2$ is

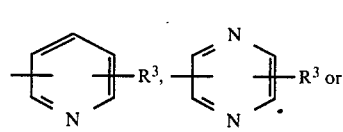

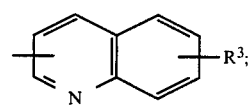

where $R^3$ is hydrogen, alkyl of 1 to 4 carbon atoms, alkoxy of 1 to 4 carbon atoms, $-CO_2R^4$ where $R^4$ is alkyl of 1 to 4 carbon atoms, halogen, cyano or nitro;
$R^5$ is hydrogen, phenyl or halophenyl;
$R^6$ is hydrogen, phenyl or halophenyl, with the proviso that one of $R^5$ and $R^6$ is other than hydrogen;
and n is one of the integers 2, 3 or 4;
or a pharmaceutically acceptable salt thereof.

In the preceding descriptions of the compounds of this invention, the term, "halogen" is intended to embrace chlorine, bromine and fluorine and the pharmaceutically acceptable salts are those derived from such organic and inorganic acids as: acetic, lactic, citric, tartaric, succinic, maleic, malonic, gluconic, hydrochloric, hydrobromic, phosphoric, nitric, sulfuric, methanesulfonic, and similarly known acceptable acids.

The compounds of this invention are readily prepared by a variety of conventional methods generally involving alkylation at 2-position of appropriately substituted gamma-carboline. For example, in Scheme 1, an appropriately substituted γ-carboline II may be reacted with either haloalklpyridine, haloalkylpyrazine, haloalkylguinoline or haloalkylquinoxaline III (route 1a) or a vinylpyridine, vinylpyrazine, vinylquinoline or vinylquinoxaline IV, (route 1b) in which $R^1$, $R^2$, $R^5$, $R^6$ and n are as previously defined.

Scheme 1

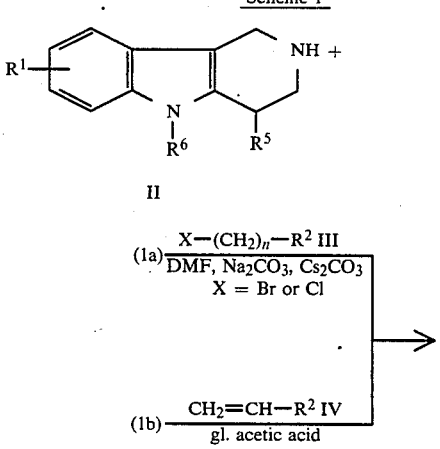

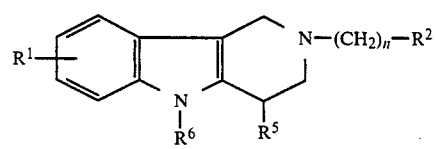

The nucleophilic substitution reaction (1a) is run in an aprotic solvent, such as dimethylformamide (DMF), dimethylsulfoxide (DMSO), acetone or alcoholic acetonitrile in the presence of a mild base such as sodium, potassium or cesium carbonate or a combination of two different carbonates.

The vinyl Michael addition reaction (1b) may be used where compounds of the invention having n=2 are desired. The reactions are conveniently run in an alcoholic solvent, preferably methanol or ethanol, in the presence of a catalytic amount of glacial acetic acid. These reactions are preferably run at solvent reflux temperatures for 24–48 hours.

The starting γ-carboline II in Scheme 1 (above) are prepared from substituted phenylhydrazines and N-carbethoxy-4-piperidone as shown in Scheme 2 (See Ebnother et al., Helv. Chim. Acta, 52, 629, 1969).

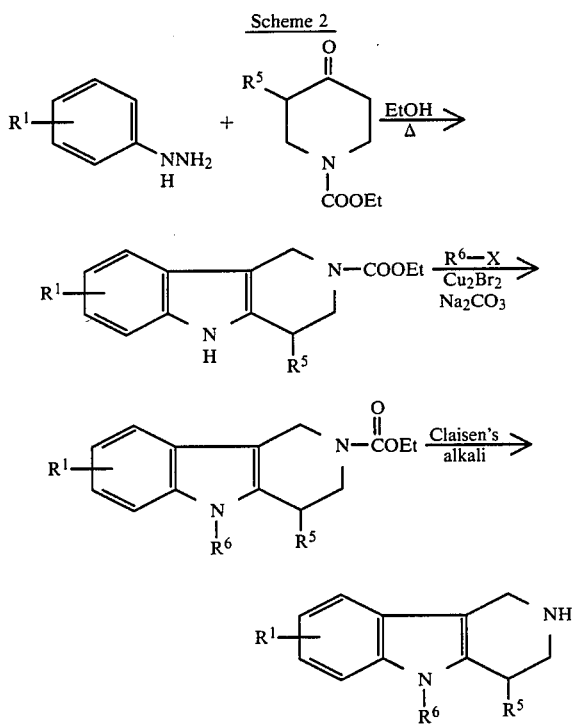

Alternatively, γ-carboline II where $R^5$ is phenyl or substituted phenyl may be prepared as shown in Scheme 3.

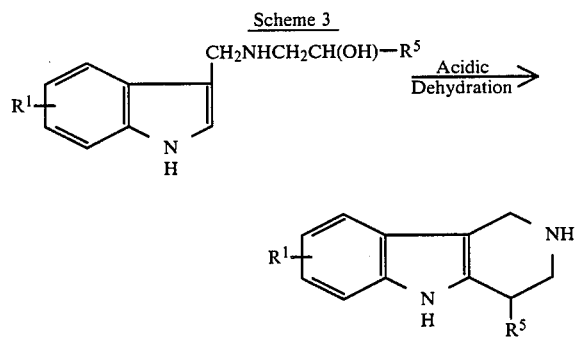

In Scheme 3, the starting indole aminoalcohols are prepared by the methods of Walker et al., J. Org. Chem. 26, 432 (1961). The ring closure step is accomplished under acidic conditions with a variety of dehydrating agents, such as trifluoroacetic acid, hydrobromic acid or preferably with sulfuric acid.

The antipsychotic properties of the compounds of this invention were established by standard pharmacologically accepted procedures involving two conditioned avoidance studies in which trained male CD rats (Charles River), 400–450 gm body weight are exposed to a fifteen second warning tone (conditioned stimulus) continued for an additional fifteen seconds accompanied by electric shock. The rat can avoid the electric shock by depression of a response lever (lever-response) or in a different study by jumping to an exposed shelf (shelf-jump response). In either test situation, a response during the initial warning tone is considered an avoidance response while a response during shock delivery is considered an escape response. The avoidance response is determined and expressed as a percentage of total trials from an appropriate number of trials and a 50% block in avoidance responding ($AB_{50}$) is obtained from a dose-effect regression line. All the data is based upon (mg/kg) dosing of the animals. The shelf-jump response test procedure follows that of Herman et al., Comm. in Psychopharm., 3, pp. 165–171 (1979).

As a measure of extrapyramidal side effects, the compounds of this invention were studied as antagonists of apomorphine-induced stereotyped behavior wherein CF-1 mice (Charles River) receive the test compound i.p. (six mice per dose level) and thirty minutes later receive 10 mg/kg apomorphine s.c. Five minutes after injection, the rearing-head-bobbing-licking syndrome induced by apomorphine is evaluated as present or absent for each animal. Readings are repeated every five minutes during a thiry minute test session. An $ED_{50}$ value (with 95% confidence intervals) is calculated for inhibition of apomorphine-induced stereotyped behavior by simple linear regression analysis. The compounds of this invention were inactive in this study, with the exception of the product of Example 5, which demonstrated a$ED_{50}$ at 1.62 mg/kg i.p. Thus, the compounds of this invention demonstrate a low potential for side-effects attending long term treatment with such standard antipsychotic drugs as haloperidol and chlorpromazine.

In further support of the low potential for side-effects exhibited by the compounds of this invention, the compounds were tested in accordance with a modification of the procedure of Fields et al., Brain Res., 136, pp. 578–584 (1977) and Yamamura et al., eds., Neurotransmitter Receptor Binding, Raven Press, N.Y. (1978), wherein homogenized limbic brain tissue is incubated with $^3$H-spiroperidol and various concentrations of test compound, filtered and washed and shaken with Hydrofluor scintillation cocktail (National Diagnostics) and counted in a Packard 460CD scintillation counter. Binding in the presence of the test compound is expressed as a percent of specific binding (total binding less binding in the presence of 1 μM (+)butaclamol). An inhibition constant ($K_i$) is calculated for each test compound to categorize its limbic D-2 binding potential. The larger the number, the less potential for dopamine receptor binding and attendant side effects from administration of the antipsychotic agent. Inhibition constants (95% confidence interval) for standard antipsychotics are:

haloperidol-4.0 (3.0–5.6)nM;
clozapine-34 (23–54)nM;
fluphenazine-4.5 (3.6–5.6)nM; and
sulpiride-376 (174–5000)nM From these data, the activity profile of the compounds of this invention are seen to be that of antipsychotic agents with much lower potential for extra pyramidal side effects such as attend the use of major tranquillizers (sedation, pseudoparkinsonism, ataxia, muscle relaxation, etc.). This activity profile resembles that of the anxiolytic compound, buspirone.

Hence, the compounds of this invention are antipsychotic agents and anxiolytic agents useful in the treatment of psychoses such as paranoia and schizophrenia and in alleviating anxiety. As such, they may be administered neat or with a pharmaceutical carrier to a patient in need thereof. The pharmaceutical carrier may be solid or liquid.

A solid carrier can include one or more substances which may also act as flavouring agents, lubricants, solubilisers, suspending agents, fillers, glidants, compression aids, binders or tablet-disintegrating agents; it can also be an encapsulating material. In powders the carrier is a finely divided solid which is in admixture with the finely divided active ingredient. In tablets the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilisers, emulsifiers, buffers, preservatives, sweeteners, flavouring agents, suspending agents, thickening agents, colours, viscosity regulators, stabilisers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. When the compound is orally active it can be administered orally either in liquid or solid composition form.

Preferably the pharmaceutical composition is in unit dosage form, e.g. as tablet or capsules. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The dosage to be used in the treatment of a specific psychosis must be subjectively determined by the attending physician. The variables involved include the specific psychosis or state of anxiety and the size, age and response pattern of the patient.

The following examples illustrate the production of compounds of this invention. After each example the pharmacological evaluation for the compound produced is presented. The conditioned avoidance tests are reported as relative activity for the shelf-jump (S-J) at the intraperitoneal (i.p.) dose administered in mg/kg and the $AB_{50}$ is presented for the lever-response (L-R) test at the oral (p.o.) dose in mg/kg. The inhibition constant is reported for limbic D-2 binding expressed in nM concentration. All of the compounds, except that of Example 5 as noted, supra, were inactive as apomorphine antagonists.

EXAMPLE 1

8-Fluoro-5-(4-fluorophenyl)-2,3,4,5-tetrahydro-2-[2-(2-pyridinyl) ethyl]-1H-pyrido[4,3-b]indole A mixture of 8-fluoro-5-(4-fluorophenyl)-2,3,4,5-tetrahydro-1H-pyrido[4,3-b]indole (3 g, 0.01 mole), 2-vinylpyridine (1.7 g, 0.01 mol) and 2 mL of glacial acetic acid were refluxed for 48 hours in 30 mL of methanol. The solvent was removed in vacuo and the separated solid was purified by HPLC using ethyl acetate as the eluant to afford 3.5 g (89.9% yield) of the title compound. It was converted to the dihydrochloride salt; mp. 267°–270° C.

Analysis for: $C_{24}H_{21}N_3F_2 \cdot 2HCl \cdot \frac{1}{4}H_2O$: Calculated: C, 61.74; H, 5.07; N, 9.0, Found: C, 61.66; H, 4.87; N, 8.92

S-J Active (20)

L-R Active (20 p.o.); 6.30 p.o. (4.18–10.25).

Linbic D-2 7 (4–11)

EXAMPLE 2

2,3,4,5-Tetrahydro-4-phenyl-2-[4-(4-pyridinyl)butyl]-1H-pyrido[4,3-b]indole

Concentrated sulfuric acid (72 mL) was stirred and cooled to 0° C. in an ice-methanol bath. α-[(1H-indol-3-ylmethyl-amino)methyl]benzyl alcohol, 22.5 g (0.08 mol) was added in small portions to the stirred cooled sulfuric acid reaction mixture over 2 hours. The cooling bath was removed and the reaction was stirred at room temperature for 5 hours. Then the reaction mixture was poured onto crushed ice, basified with 50% aqueous sodium hydroxide solution (with ice cooling). Ethyl acetate was added and the basic mixture stirred well until two clear phases resulted. The aqueous phase was extracted several more times with ethyl acetate, the combined extracts washed with water and dried over anhydrous sodium sulfate. The extract after filtration was evaporated in vacuo and the residue dissolved in hot benzene, filtered hot and allowed to crystallize to obtain 10.0 g of 2,3,4,5-tetrahydro-4-phenyl-1H-pyrido[4,3-b]indole, m.p. 135°–155° C.

An analytical sample of the maleate salt was obtained from ethyl acetate and recrystallized from isopropanol; m.p. 170.5° C. (dec).

Analysis for: $C_{17}H_{16}N_2 \cdot C_4H_4O_4$: Calculated: C, 69.22, H, 5.53; N, 7.69; Found: C, 68.88; H, 5.56; N, 7.49

To a stirred suspension of 2,3,4,5-tetrahydro-4-phenyl-1H-pyrido[4,3-b]indole (2 g, 0.008 mole), freshly baked anhydrous sodium carbonate (1.7 g, 0.016 mol) and a catalytic amount of cesium carbonate in 70 mL of dimethylformamide, was added 2.4 g (0.016 mol) of 4-pyridinyl-butylbromide hydrobromide. The reaction was stirred overnight at room temperature, then the solvent was removed under vacuum and the solid cake was suspended in 100 mL of water and extracted with methylene chloride (3×100 mL). The methylene chloride extracts were combined, dried over anhydrous sodium sulfate and evaporated under reduced pressure.

The title compound was separated by HPLC using ethyl acetate as the eluant to afford 1.1 g (36% yield). It was converted to the dihydrochloride hemihydrate; mp 228°–230° C.

Analysis for: $C_{26}H_{27}N_3.2HCl.\frac{1}{2}H_2O$: Calculated: C, 67.38; H, 6.47; N, 9.07; Found: C, 67.30; H, 6.48; N, 9.10
S-J Very weak (20)
Limbic D-2 404 (231–757)

EXAMPLE 3

2,3,4,5-Tetrahydro-4-phenyl-2-[3-(3-pyridinyl)propyl]-1H-pyrido[4,3-b]indole

The title compound was prepared following the procedure of Example 2 with the exception that 3-pyridinylpropyl bromide hydrobromide was used instead of 4-pyridinylbutyl bromide hydrobromide. The product was converted to the dihydrochloride hydrate; mp 204°–206° C.

Analysis for: $C_{25}H_{25}N_3.2HCl.H_2O$: Calculated: C, 65.5; H, 6.37; N, 9.16; Found: C, 66.13; H, 6.23; N, 9.16
S-J >20 mg/kg
Limbic D-2 140 (70–270)

EXAMPLE 4

2,3,4,5-Tetrahydro-4-phenyl-2-[2-(2-pyridinyl)ethyl]-1H-pyrido[4,3-b]indole

The title compound was prepared following the procedure of Example 1 with the exception that 2,3,4,5-tetrahydro-4-phenyl-1H-pyrido[4,3-b]indole was used instead of 8-fluoro-5-(4-fluorophenyl)-2,3,4,5-tetrahydro-1H-pyrido[4,3-b]indole. The product was converted to the dihydrochloride salt; mp 190°–192° C.

Analysis for: $C_{24}H_{23}N_3.2HCl.1\frac{1}{2}H_2O$: Calculated: C, 63.58; H, 6.22; N, 9.27; Cl, 15.64; Found: C, 64.02; H, 6.06; N, 9.11; Cl, 15.46
S-J >10 mg/kg
Limbic D-2 600 (220–3100)

EXAMPLE 5

8-Fluoro-5-(4-fluorophenyl)-2,3,4,5-tetrahydro-2-[2-(2-quinolinyl)ethyl]-1H-pyrido[4,3-b]indole The title compound was prepared following the procedure of Example 1 with the exception that 2-vinylquinoline was used instead of 2-vinylpyridine. The product was converted to the dihydrochloride salt; mp 201°–203° C.

Analysis for: $C_{28}H_{23}F_2N_3.2HCl.1\frac{1}{4}H_2O$: Calculated: C, 65.30; H, 4.95; N, 8.16; Found: C, 64.14; H, 4.86; N, 8.45
S-J Active (40 i.p.)
L-R Active (40 p.o.)
Limbic D-2 1.07 (0.75–1.47)

EXAMPLE 6

8-Fluoro-5-(4-fluorophenyl)-2,3,4,5-tetrahydro-2-[4-(2-pyridinyl)butyl]-2H-pyrido[4,3-b]indole The title compound was prepared following the procedure of Example 2 with the exception that 8-fluoro-2,3,4,5-tetrahydro-1H-pyrido[4,3-b]indol was used instead of 2,3,4,5-tetrahydro-4-phenyl-1H-pyrido[4,3-b]indole. The product was converted to the dihydrochloride salt; mp 178°–180° C.

Analysis for: $C_{26}H_{25}F_2N_3.2HCl.2H_2O$: Calculated: C, 59.3; H, 5.9; N, 7.98; Found: C, 58.93; H, 5.31; N, 7.8
S-J Active (40 i.p.)

EXAMPLE 7

8-Fluoro-5-(4-fluorophenyl)-2,3,4,5-tetrahydro-2-[2-(4-pyridinyl)ethyl]-1H-pyrido[4,3-b]indole The title compound was prepared following the procedure of Example 1 with the exception that 4-vinylpyridine was used instead of 2-vinylpyridine. The product was converted to the dihydrochloride salt; mp 246°–248° C.

Analysis for: $C_{24}H_{21}F_2N_3.2HCl.\frac{1}{4}H_2O$: Calculated: C, 61.69; H, 5.03; N, 8.99; Found: C, 61.76; H, 5.08; N, 8.70
S-J Active (40 i.p.)
Limbic D-2 12 (9–19)

EXAMPLE 8

8-Fluoro-5-(4-fluorophenyl)-2,3,4,5-tetrahydro-2-[2-(2-pyrazinyl)ethyl]-1H-pyrido[4,3-b]indole The title compound was prepared following the procedure of Example 1 with the exception that 2-vinylpyrazine was used instead of 2-vinylpyridine. The product was converted to the dihydrochloride salt; mp 197°–199° C.

Analysis for: $C_{23}H_{20}F_2N_4.2HCl$: Calculated: C, 59.61; H, 4.78; N, 12.09; Found: C, 59.17; H, 4.77; N, 12.12
S-J Very Active (40 i.p.)
L-R Active (20 p.o.); 15.2 (8.27–35.25)

What is claimed is:

1. A compound of the formula:

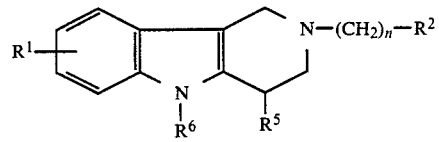

in which
$R^1$ is hydrogen, halogen, hydroxy or alkyl of 1 to 6 carbon atoms;
$R^2$ is

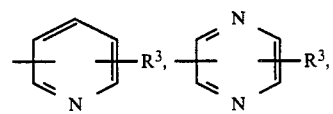

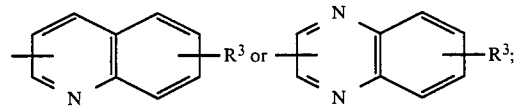

where R³ is hydrogen, alkyl of 1 to 4 carbon atoms, alkoxy of 1 to 4 carbon atoms, —CO₂R⁴ where R⁴ is alkyl of 1 to 4 carbon atoms, halogen, cyano or nitro;

R⁵ is hydrogen, alkyl of 1 to 6 carbon atoms, phenyl, or phenyl substituted by a halogen, methyl, trifluoromethyl, cyano or nitro group;

R⁶ is hydrogen, phenyl, or phenyl substituted by a methyl, ethyl, methoxy, ethoxy, halogen, trifluoromethyl, cyano or nitro group; with the proviso that one of R⁵ and R⁶ is other than hydrogen;

and n is one of the integers 1 to 7;

or a pharmaceutically acceptable salt thereof.

2. A compound of claim 1 of the formula:

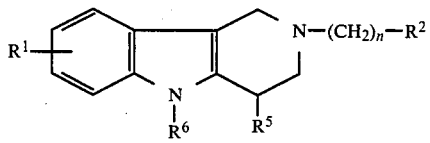

in which
R¹ is hydrogen or halogen;
R² is

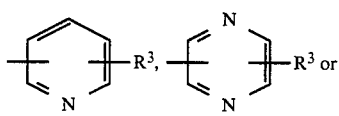

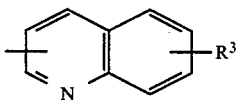

where R³ is hydrogen, alkyl of 1 to 4 carbon atoms, alkoxy of 1 to 4 carbon atoms, —CO₂R⁴ where R⁴ is alkyl of 1 to 4 carbon atoms, halogen, cyano or nitro;

R⁵ is hydrogen, phenyl or halophenyl;
R⁶ is hydrogen, phenyl or halophenyl, with the proviso that one of R⁵ and R⁶ is other than hydrogen;
and n is one of the integers 2, 3 or 4;
or a pharmaceutically acceptable salt thereof.

3. The compound of claim 1 which is 8-fluoro-5-(4-fluorophenyl)-2,3,4,5-tetrahydro-2-[2-(2-pyridinyl)ethyl]-1H-pyrido[4,3-b]indole or a pharmaceutically acceptable salt thereof.

4. The compound of claim 1 which is 2,3,4,5-tetrahydro-4-phenyl-2-[4-(4-pyridinyl)butyl]-1H-pyrido[4,3-b]indole or a pharmaceutically acceptable salt thereof.

5. The compound of claim 1 which is 2,3,4,5-tetrahydro-4-phenyl-2-[3-(3-pyridinyl)propyl]-1H-pyrido[4,3-b]indole or a pharmaceutically acceptable salt thereof.

6. The compound of claim 1 which is 2,3,4,5-tetrahydro-4-phenyl-2-[2-(2-pyridinyl)ethyl]-1H-pyrido[4,3-b]indole or a pharmaceutically acceptable salt thereof.

7. The compound of claim 1 which is 8-fluoro-5-(4-fluorophenyl)-2,3,4,5-tetrahydro-2-[2-(2-quinolinyl)ethyl]-1H-pyrido[4,3-b]indole or a pharmaceutically acceptable salt thereof.

8. The compound of claim 1 which is 8-fluoro-5-(4-fluorophenyl)-2,3,4,5-tetrahydro-2-[4-(2-pyridinyl)butyl]-2H-pyrido[4,3-b]indole or a pharmaceutically acceptable salt thereof.

9. The compound of claim 1 which is 8-fluoro-5-(4-fluorophenyl)-2,3,4,5-tetrahydro-2-[2-(4-pyridinyl)ethyl]-1H-pyrido[4,3-b]indole or a pharmaceutically acceptable salt thereof.

10. The compound of claim 1 which is 8-fluoro-5-(4-fluorophenyl)-2,3,4,5-tetrahydro-2-[2-(2-pyrazinyl)ethyl]-1H-pyrido[4,3-b]indole or a pharmaceutically acceptable salt thereof.

* * * * *